United States Patent [19]

Bitha et al.

[11] Patent Number: 4,833,270

[45] Date of Patent: May 23, 1989

[54] PROCESS FOR PREPARING 2-CHLORO-4,5-DIFLUOROBENZOIC ACID

[75] Inventors: Panayota Bitha, Nanuet; Yang-I Lin, Tappan, both of N.Y.

[73] Assignee: American Cyanamid Company, Stamford, Conn.

[21] Appl. No.: 136,052

[22] Filed: Dec. 21, 1987

[51] Int. Cl.$^4$ ............................................. C07C 51/363
[52] U.S. Cl. .................................... 562/493; 548/485; 562/456; 562/458; 564/194
[58] Field of Search ...................... 564/194; 548/485; 502/456, 458, 473

[56] References Cited

U.S. PATENT DOCUMENTS

| | | | |
|---|---|---|---|
| 2,542,812 | 2/1951 | Hartung | 564/194 |
| 3,905,800 | 9/1975 | Dominy et al. | 71/92 |
| 4,322,533 | 3/1982 | Lesher et al. | 514/930 |
| 4,439,620 | 3/1984 | Klauke et al. | 562/493 |
| 4,521,616 | 6/1985 | Fifalt et al. | 562/456 |

FOREIGN PATENT DOCUMENTS 0077501  4/1983  European Pat. Off. ............ 562/493

OTHER PUBLICATIONS

Fiesor et al., "Reagents for Organic Synthesis", p. 166, (1967).

Primary Examiner—James H. Reamer
Attorney, Agent, or Firm—Edward A. Conroy, Jr.

[57] ABSTRACT

This disclosure describes a novel process for preparing 2-chloro-4,5-difluorobenzoic acid which is useful in the preparation of 7-(substituted)piperazinyl-1-substituted-6-fluoro-1,4-dihydro-4-oxo-3-quinolinecarboxylic acid antibacterial agents.

1 Claim, No Drawings

PROCESS FOR PREPARING 2-CHLORO-4,5-DIFLUOROBENZOIC ACID

This invention is concerned with a process for producing 2-chloro-4,5-difluorobenzoic acid which is an intermediate used in the preparation of 1-substituted-6,7-difluoro-1,4-dihydro-4-oxo-3-quinolinecarboxylic acid which is an intermediate used in the preparation of 7-(substituted)piperazinyl-1-substituted-6-fluoro-1,4-dihydro-4-oxo-3-quinolinecarboxylic acid antibacterial agents which are disclosed in Patent No. 87/0330 of the Republic of South Africa, issued Aug. 26, 1987.

The compound 2-chloro-4,5-difluorobenzoic acid and its precursor 2-amino-4,5-difluorobenzoic acid are new compounds which may be prepared according to the following reaction scheme.

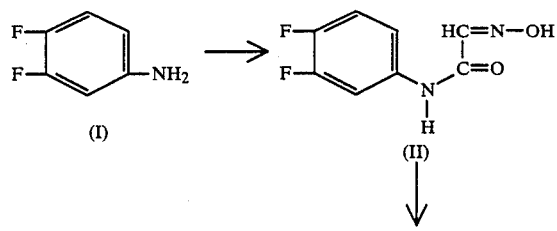

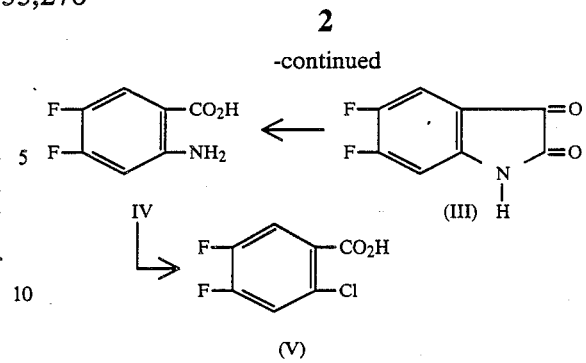

In accordance with the above reaction scheme, an aqueous solution of 3,4-difluoroaniline (I) and hydroxylamine hydrochloride containing hydrochloric acid is reacted with an aqueous solution of chloral hydrate and sodium sulfate at the reflux, then filtered while hot, giving N-(3,4-difluorophenyl)-2-(hydroxyimino)-acetamide (II). The compound (II) is reacted with concentrated sulfuric acid with heat, then added to cracked ice, giving 5,6-difluoro-1H-indole-2,3-dione (III). A basic aqueous solution of compound (III) is treated with hydrogen peroxide and heat, then cooled and acidified, giving 2-amino-4,5-difluorobenzoic acid (IV). The compound (IV) is added to a mixture of anhydrous copper-(II) chloride, t-butyl nitrite and anhydrous acetonitrile at 0°–5° C., then added to a dilute mineral acid, giving 2-chloro-4,5-difluorobenzoic acid (V).

Compound (V) may then be reacted according to the following reaction scheme to produce the aforementioned intermediate 1-cyclopropyl-6,7-difluoro-1,4-dihydro-4-oxo-3-quinolinecarboxylic acid.

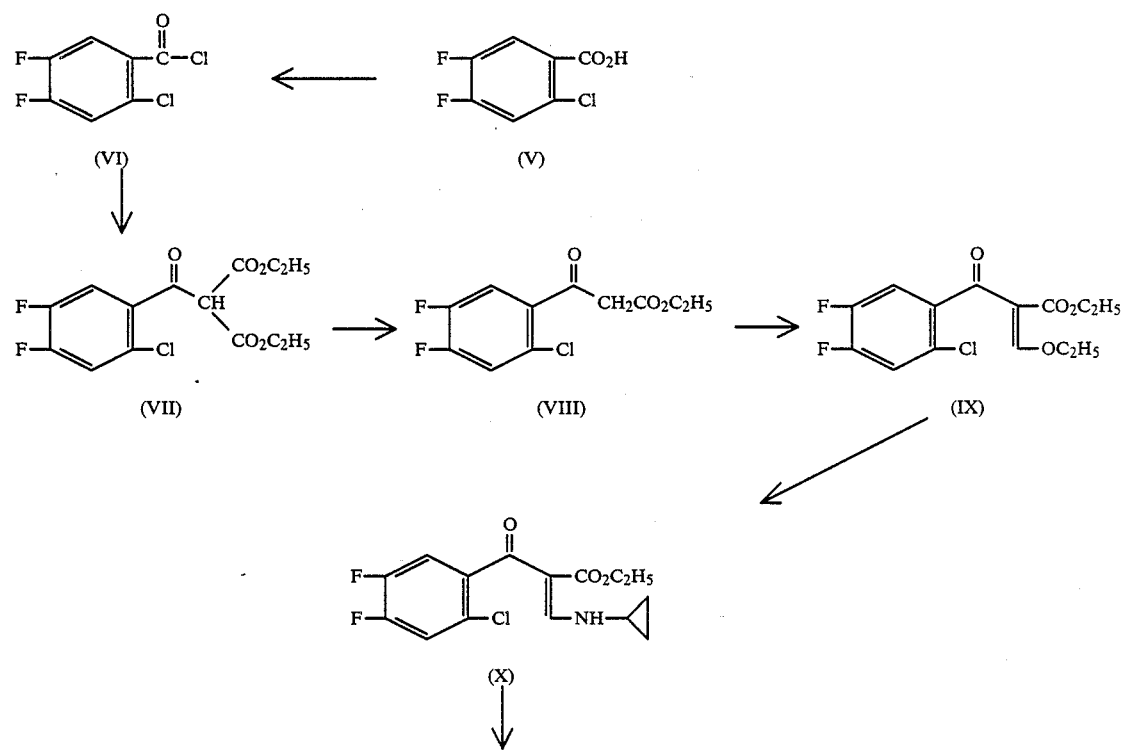

-continued

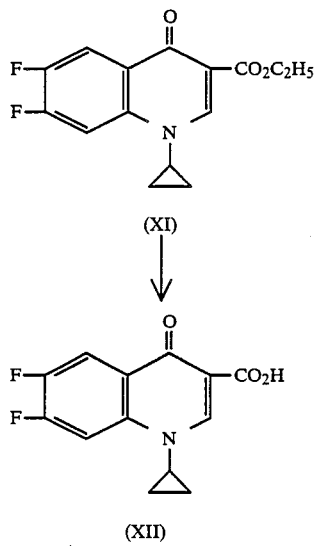

In accordance with the above reaction scheme, a solution of 2-chloro-4,5-difluorobenzoic acid (V) in acetonitrile containing a catalytic amount of dimethylformamide is reacted under an inert atmosphere with the dropwise addition of oxalyl chloride, giving 2-chloro-4,5-difluorobenzoic acid chloride (VI) which is dissolved in diethyl ether and slowly added to a cold solution of magnesium diethylmalonate, followed by the addition to ice water and acidification to pH 2.5, giving (2-chloro-4,5-difluorobenzoyl)propanedioic acid diethyl ester (VII). A solution of compound (VII) in p-dioxane and water is heated at reflux, then evaporated and distilled, giving 2-chloro-4,5-difluoro-$\beta$-oxobenzenepropanoic acid ethyl ester (VIII). A solution of compound (VIII) and triethyl orthoformate in acetic anhydride is heated at 150° C. for 2 hours, giving 2-chloro-$\alpha$-(ethoxymethylene)-4,5-difluoro-$\beta$-oxobenzenepropanoic acid, ethyl ester (IX). Cyclopropylamine is added to a solution of compound (IX) in ethanol, giving 2-chloro-$\alpha$-[(cyclopropylamino)methylene]-4,5-difluoro-$\beta$-oxobenzenepropanoic acid, ethyl ester (X). Compound (X) is reacted with sodium hydride in dry dimethylformamide under an inert atmosphere with heat, giving 1-cyclopropyl-6,7-difluoro-1,4-dihydro-4-oxo-3-quinolinecarboxylic acid, ethyl ester (XI). Ester (XI) is then refluxed with acid, giving the desired 1-cyclopropyl-6,7-difluoro-1,4-dihydro-4-oxo-3-quinolinecarboxylic acid (XII).

This invention is further described by the following specific examples.

EXAMPLE 1

N-(3,4-Difluorophenyl)-2-(hydroxyimino)acetamide

A solution of 18.2 g of chloral hydrate and 260 g of anhydrous sodium sulfate in 400 ml of water was mixed with a solution of 12.9 g of 3,4-difluoroaniline and 22.24 g of hydroxylamine hydrochloride in 160 ml of water and 9 ml of concentrated hydrochloric acid. This reaction mixture was refluxed for 2 hours and then filtered while hot, collecting the solid which was washed well with water and dried. Recrystallization from hot water gave 8.4 g of the desired compound as colorless crystals, mp 148°–150° C.

EXAMPLE 2

5,6-Difluoro-1H-indole-2,3-dione

A 24.5 g portion of N-(3,4-difluorophenyl)-2-(hydroxyimino)acetamide was added portionwise with stirring to 95 ml of concentrated sulfuric acid with the temperature kept between 60° and 70° C. The temperature of the reaction mixture was then raised to 80° C. for 20 minutes followed by cooling to room temperature. The mixture was then poured onto crushed ice and the resulting solid collected, giving 21.3 g of the desired compound as brick red crystals, mp 218°–220° C.

EXAMPLE 3

2-Amino-4,5-difluorobenzoic acid

A solution of 20 g of 5,6-difluoro-1H-indole-2,3-dione in 200 ml of 2.5N sodium hydroxide was treated dropwise with 35.7 ml of 31.4% hydrogen peroxide. The reaction mixture was warmed to 80° C. for 15 minutes, then treated with charcoal and filtered. The filtrate was cooled in an ice bath and acidified with hydrochloric acid to pH 3.5. The resulting precipitate was crystallized from xylene, giving 14.18 g of the desired compound mp 176°–178° C.

EXAMPLE 4

2-Chloro-4,5-difluorobenzoic acid

A 12.19 g portion of anhydrous copper(II) chloride, 12.37 g of t-butyl nitrite and 360 ml of anhydrous acetonitrile were added to a three-necked round bottom flask. This mixture was stirred rapidly and cooled to 0°–5° C., then 13.7 g of 2-amino-4,5-difluorobenzoic acid was added slowly over a period of 5 minutes. The reaction mixture was stirred in the cold for 2 hours, then at room temperature overnight, concentrated to about ½ its volume and poured into 200 ml of 6N hydrochloric acid. The desired compound was extracted in ether and then further purified by dissolving it in water, adjusting then pH to 8 with sodium bicarbonate, extracting the colored impurities with ether, acidifying the aqueous phase to pH 2 with hydrochloric and finally extracting the desired compound in ether, giving 11.5 g of light yellow crystals, mp 86°–88° C.

EXAMPLE 5

(2-Chloro-4,5-difluorobenzoyl)propanedioic acid, diethyl ester

A 32.8 g portion of 2-chloro-4,5-difluorobenzoic acid was dissolved in 175 ml of dry acetonitrile containing a catalytic amount (2 drops) of dimethylformamide. A 25.3 ml portion of oxalyl chloride was added dropwise under a nitrogen atmosphere through an addition funnel and the reaaction was stirred under nitrogen for 30 minutes, then evaporated to dryness. The oily residue was dissolved in 30 ml of toluene and then evaporated under reduced pressure, giving 2-chloro-4,5-difluorobenzonic acid chloride as an oil. This oil was dissolved in 200 ml of anhydrous diethyl ether and slowly added to a cold ($-5°$ to $-10°$ C.) solution of magnesium diethylmalonate (prepared by stirring 4.97 g of magnesium turnings in 515 ml of ethanol containing 15 ml of carbon tetrachloride under nitrogen, then slowly adding a solution of 32.7 g of diethylmalonate in a mixture of 40 ml of ethanol and 15 ml of ether, refluxing the suspension under nitrogen for 2 hours until all the magnesium dissolved). The reaction mixture was stirred at $-10°$ C. for 1 hour and then allowed to warm to room temperature overnight. A 300 ml portion of ice water was addded and the pH adjusted to 2.5 with 6 ml of sulfuric acid. The suspension was concentrated in vacuo to about 300 ml and the separated oily phase removed, heated at 60° C. in vacuo and distilled in a Kugelrohr at 110°-130° C., giving 26.5 g of the desired compound as a bright yellow oil.

EXAMPLE 6

2-Chloro-4,5-difluoro-$\beta$-oxobenzenepropanoic acid, ethyl ester

A solution of 25.5 g of (2-chloro-4,5-difluorobenzoyl)propanedioic acid, diethyl ester in 500 ml of p-dioxane and 2.74 ml of water was refluxed for 3 hours, then evaporated to dryness and distilled on a Kugelrohr, giving 14.6 g of the desired compound as a bright yellow oil.

EXAMPLE 7

2-Chloro-$\alpha$-(ethoxymethylene)-4,5-difluoro-$\beta$-oxobenzenepropanoic acid, ethyl ester A solution of 14.5 g of 2-chloro-4,5-difluoro-$\beta$-oxobenzenepropanoic acid, ethyl ester and 12.27 g of triethyl orthoformate in 13 ml of acetic anhydride was heated at 150° C. for 2 hours and then evaporated to dryness, giving 16.59 g of the desired product as an oil.

EXAMPLE 8

2-Chloro-$\alpha$-[(cyclopropylamino)methylene]-4,5-difluoro-$\beta$-oxobenzenepropanoic acid, ethyl ester A 3.9 ml portion of cyclopropylamine was added dropwise to a solution of 16.25 g of 2-chloro-$\alpha$-(ethoxymethylene)-4,5-difluoro-$\beta$-oxobenzenepropanoic acid, ethyl ester in 45 ml of ethanol, producing an exotherm. The solution was stirred for 1 hour, evaporated to dryness and the residue crystallized from hexane, giving 14.6 g of the desired compound, mp 55°-58° C.

EXAMPLE 9

1-Cyclopropyl-6,7-difluoro-1,4-dihydro-4-oxo-3-quinolinecarboxylic acid, ethyl ester A 3.06 g portion of 50% sodium hydride in oil was washed in hexane, the organic phase decanted and the sodium hydride slurried in 150 ml of dry dimethylformamide. To this suspension, under nitrogen, was added a solution of 14 g of 2-chloro-$\alpha$-[(cyclopropylamino)-methylene-4,5-difluoro-$\beta$-oxobenzenepropanoic acid, ethyl ester in 50 ml of dimethylformamide. The reaction mixture was stirred at room temperature for 30 minutes, then at 100° C. for 30 minutes and then evaporated to dryness. The residue was slurried in water, the solid collected and crystallized from methanol, giving 5 g of the desired compound, mp 202°-204° C.

EXAMPLE 10

1-Cyclopropyl-6,7-difluoro-1,4-dihydro-4-oxo-3-quinolinecarboxylic acid

A solution of 6,8 g of 1-cyclopropyl-6,7-difluoro-1,4-dihydro-4-oxo-3-quinolinecarboxylic acid, ethyl ester in a mixture of 46 ml of glacial acetic acid, 35 ml of water and 4.5 ml of concentrated sulfuric acid was refluxed for 1.5 hours. The resulting suspension was cooled in an ice bath, the solid collected, washed with cold water, dried and recrystallized from hot dimethylformamide, giving 5 g of the desired compound, mp 288°-290° C.

We claim:

1. A process for producing 2-chloro-4,5-difluorobenzoic acid which comprises reacting 3,4-difluoroaniline and hydroxylamine hydrochloride in an aqueous acidic solution with an aqueous solution of chloral hydrate and sodium sulfate at reflux, filtering while hot, giving N-(3,4-difluorophenyl)-2-(hydroxyimino)acetamide, which is reacted with concentrated sulfuric acid and heat, giving 5,6-difluoro-1H-indole-2,3-dione, which is dissolved in an aqueous base, treated with hydrogen peroxide and heat, then cooled and acidified, giving 2-amino-4,5-difluorobenzoic acid, which is reacted with anhydrous copper(II) chloride, t-butyl nitrite and anhydrous acetonitrile at 0°-5° C., then added to a dilute mineral acid, giving the desired compound.

* * * * *